(12) United States Patent
Zank et al.

(10) Patent No.: US 9,476,953 B1
(45) Date of Patent: Oct. 25, 2016

(54) NUCLEAR QUADRUPOLE RESONANCE SYSTEM

(71) Applicant: BAE Systems Information And Electronic Systems Integration Inc., Nashua, NH (US)

(72) Inventors: Paul A. Zank, Brookline, NH (US); David H. Herlihy, Nashua, NH (US); Eldon M. Sutphin, Merrimack, NH (US); Roland A. Gilbert, Milford, NH (US); Paul E. Gili, Mason, NH (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 630 days.

(21) Appl. No.: 13/975,877

(22) Filed: Aug. 26, 2013

Related U.S. Application Data

(60) Provisional application No. 61/692,819, filed on Aug. 24, 2012, provisional application No. 61/692,858, filed on Aug. 24, 2012.

(51) Int. Cl.
*G01R 33/36* (2006.01)

(52) U.S. Cl.
CPC .................................. *G01R 33/3692* (2013.01)

(58) Field of Classification Search
CPC .................................................. G01R 33/3692
See application file for complete search history.

(56) References Cited

U.S. PATENT DOCUMENTS

| | | | |
|---|---|---|---|
| 3,641,440 A | 2/1972 | Bush | |
| 4,352,180 A | 9/1982 | Schulze | |
| 4,513,292 A | 4/1985 | Bowman | |
| 5,076,993 A | 12/1991 | Sawa et al. | |
| 5,166,615 A | 11/1992 | Sidles | |
| 5,206,592 A | 4/1993 | Buess et al. | |

(Continued)

FOREIGN PATENT DOCUMENTS

| | | |
|---|---|---|
| EP | 0813685 | 10/1996 |
| EP | 1801607 | 6/2007 |

(Continued)

OTHER PUBLICATIONS

Mool Chand Gupta, Book titled Atomic and molecular spectroscopy, 2001, p. 388.*

(Continued)

*Primary Examiner* — G. M. Hyder
(74) *Attorney, Agent, or Firm* — Sand & Sebolt, LPA; Daniel J. Long; Scott J. Asmus

(57) ABSTRACT

A system and method for detecting at least one material under test (MUT) is presented. A Nuclear Quadrupole Resonance (NQR) measurement system includes a waveform generator configured to generate a continuous wave (CW) input signal comprising one or more frequencies. An RF shielded chamber receives the at least one MUT that is carried by a person walking through the chamber. A probe within the chamber illuminates the MUT with the CW signal and simultaneously receives possible NQR emissions from the at least one MUT. A bridge circuit is utilized to cancel the strong excitation CW signal from the generator which would otherwise mask the weak NQR emissions from the MUT that are received and detected by the measurement system. A detector can then detect the MUT based, at least in part, on the resonance signal.

18 Claims, 4 Drawing Sheets

(56) References Cited

U.S. PATENT DOCUMENTS

| | | | |
|---|---|---|---|
| 5,233,300 A | 8/1993 | Buess et al. | |
| 5,539,412 A | 7/1996 | Mendelson | |
| 5,594,338 A | 1/1997 | Magnuson | |
| 5,608,321 A | 3/1997 | Garroway et al. | |
| 6,046,586 A | 4/2000 | Rinard | |
| 6,054,856 A | 4/2000 | Garroway et al. | |
| 6,100,688 A | 8/2000 | Smith et al. | |
| 6,104,190 A | 8/2000 | Buess et al. | |
| 6,166,541 A | 12/2000 | Smith et al. | |
| 6,194,898 B1 | 2/2001 | Magnuson et al. | |
| 6,411,835 B1 | 6/2002 | Modell et al. | |
| 6,486,838 B1 * | 11/2002 | Smith | G01R 33/441 324/300 |
| 6,777,937 B1 | 8/2004 | Miller et al. | |
| 6,822,444 B2 | 11/2004 | Lai | |
| 6,900,633 B2 | 5/2005 | Sauer et al. | |
| 7,106,244 B2 | 9/2006 | Hsu | |
| 7,119,682 B1 | 10/2006 | Fisher | |
| 7,142,109 B1 | 11/2006 | Frank | |
| 7,151,447 B1 | 12/2006 | Willms et al. | |
| 7,170,288 B2 | 1/2007 | Fullerton | |
| 7,188,513 B2 | 3/2007 | Wilson | |
| 7,265,550 B2 | 9/2007 | Laubacher et al. | |
| 7,292,033 B2 | 11/2007 | Pusiol | |
| 7,345,478 B2 | 3/2008 | Lieblich et al. | |
| 7,352,180 B2 | 4/2008 | Manneschi | |
| 7,365,536 B2 | 4/2008 | Crowley et al. | |
| 7,394,250 B2 | 7/2008 | Itozaki et al. | |
| 7,394,363 B1 | 7/2008 | Ghahramani | |
| 7,397,239 B2 | 7/2008 | Crowley et al. | |
| 7,397,377 B1 | 7/2008 | Young et al. | |
| 7,417,440 B2 | 8/2008 | Peschmann et al. | |
| 7,471,744 B2 | 12/2008 | Van Wechel et al. | |
| 7,511,496 B2 | 3/2009 | Schiano | |
| 7,511,514 B2 | 3/2009 | Crowley et al. | |
| 7,511,654 B1 | 3/2009 | Goldman et al. | |
| 7,521,932 B2 | 4/2009 | Carter et al. | |
| 7,595,638 B2 | 9/2009 | Crowley | |
| 7,768,262 B2 | 8/2010 | Schiano | |
| 7,880,467 B2 | 2/2011 | Rapoport | |
| 7,888,646 B2 | 2/2011 | Breit et al. | |
| 8,463,557 B2 | 6/2013 | Apostolos et al. | |
| 8,570,038 B2 | 10/2013 | Zank et al. | |
| 8,674,697 B2 | 3/2014 | Apostolos et al. | |
| 8,710,837 B2 | 4/2014 | Zank et al. | |
| 8,773,127 B2 | 7/2014 | Apostolos et al. | |
| 8,922,211 B2 | 12/2014 | Apostolos et al. | |
| 9,052,371 B1 * | 6/2015 | Apostolos | G01R 33/441 |
| 2003/0071619 A1 | 4/2003 | Sauer et al. | |
| 2004/0138838 A1 | 7/2004 | Scheiner et al. | |
| 2004/0150550 A1 | 8/2004 | Shouno et al. | |
| 2004/0196036 A1 | 10/2004 | Lai | |
| 2004/0222790 A1 | 11/2004 | Karmi et al. | |
| 2004/0235435 A1 | 11/2004 | Barabash | |
| 2005/0059355 A1 | 3/2005 | Liu | |
| 2005/0128069 A1 * | 6/2005 | Skatter | G01V 5/0008 340/522 |
| 2005/0241639 A1 | 11/2005 | Zilberg | |
| 2006/0012371 A1 | 1/2006 | Laubacher et al. | |
| 2006/0122484 A1 | 6/2006 | Itozaki et al. | |
| 2006/0132127 A1 | 6/2006 | Fullerton | |
| 2006/0232274 A1 | 10/2006 | Shilstone et al. | |
| 2006/0261942 A1 | 11/2006 | Frank | |
| 2007/0096731 A1 | 5/2007 | Peshkovsky | |
| 2007/0153974 A1 | 7/2007 | Smith | |
| 2007/0221863 A1 | 9/2007 | Zipf | |
| 2007/0266771 A1 | 11/2007 | Goldson et al. | |
| 2008/0018332 A1 | 1/2008 | Lieblich et al. | |
| 2008/0036462 A1 | 2/2008 | Schiano | |
| 2008/0309339 A1 | 12/2008 | Chisholm et al. | |
| 2009/0039884 A1 | 2/2009 | Schiano | |
| 2009/0041187 A1 | 2/2009 | Peschmann et al. | |
| 2009/0046538 A1 | 2/2009 | Breed et al. | |
| 2009/0085565 A1 | 4/2009 | Fullerton | |
| 2009/0153346 A1 | 6/2009 | Crowley et al. | |
| 2010/0022009 A1 | 1/2010 | Yaniv | |
| 2010/0212401 A1 | 8/2010 | Crowley et al. | |
| 2011/0102597 A1 | 5/2011 | Daly et al. | |
| 2011/0187363 A1 | 8/2011 | Zank et al. | |
| 2012/0086450 A1 | 4/2012 | Crowley et al. | |
| 2012/0161771 A1 | 6/2012 | Apostolos et al. | |
| 2012/0206141 A1 | 8/2012 | Apostolos et al. | |
| 2014/0333302 A1 * | 11/2014 | Apostolos | G01N 24/084 324/309 |

FOREIGN PATENT DOCUMENTS

| | | |
|---|---|---|
| WO | 97/03366 | 1/1997 |
| WO | 2006071198 | 7/2006 |

OTHER PUBLICATIONS

U.S. Appl. No. 12/957,820.
U.S. Appl. No. 12/957,859.
U.S. Appl. No. 12/957,893.
U.S. Appl. No. 13/975,940.

* cited by examiner

NUCLEAR QUADRUPOLE RESONANCE SYSTEM

CROSS REFERENCE TO RELATED APPLICATION

This application claims priority from U.S. Provisional Patent Application Ser. No. 61/692,819, filed Aug. 24, 2012 and U.S. Provisional Patent Application Ser. No. 61/692,858, filed Aug. 24, 2012, the disclosures of which are incorporated herein by reference.

BACKGROUND OF THE INVENTION

1. Field of Invention

The current invention relates generally to apparatuses, systems and methods of detecting explosives. More particularly, the apparatuses, systems and methods relate to detecting explosives with different frequencies, and specifically, using a Nuclear Quadrupole Resonance (NQR) measurement system/device.

2. Description of Related Art

Modern day threats to the safety of people involve detonating explosives. Therefore, a variety of ways to detect explosives have been developed. For example, scanning machines have been developed to look through luggage at an airport to allow baggage screeners to see explosives and other weapons. Other screening devices are used to screen aircraft passengers. More recently NQR detection systems have been deployed to detect and identify explosives. Explosives and other compounds have unique NQR signatures that may consist of multiple NQR frequency emissions. The ability to see more than one NQR frequency from baggage or on persons improves the probability of correctly identifying explosives. Systems that do not look for multiple NQR frequencies may produce false positive results. A need, therefore, exists for an improved means for preventing false positives in NQR systems for remotely detecting explosives.

The NQR emissions from explosive substances are at a very low amplitude level compared to the RF signal that stimulated the emission. Most NQR measurement systems utilized a pulsed RE signal to stimulate the substance that will radiate NQR emissions. The measurement system produces a strong RF pulse, which could be several hundred watts, that is transmitted through a RF probe enclosed within an RE-isolated chamber that contains the package containing the suspected explosive material. Once the pulse is transmitted, the transmitter immediately shuts down, turning on circuitry to dampen probe resonances. A receiver is then turned on to listen to the weak NQR emissions from the substance. NQR emissions from nitrogen containing materials as well as other substances that produce NQR emissions exhibit an exponential decay. The receiver, if turned on quickly enough, captures the residual decaying emissions. Depending on the decay time constants of various materials, the pulse repetition rate can be slow thus preventing or limiting longer integration times to capture the emissions with stronger Signal-to-noise ratio.

A CW NQR measurement system, can pump more RF energy into those NQR frequencies at a much lower overall power, say a watt or lower. Moreover, the CW measurement system has more time to integrate over the NQR emissions from substances. In a CW NQR system, the receiver is simultaneously on while the transmitter is illuminating the package containing the suspect material. Receiver dynamic ranges exceeding 130 dB to 150 dB are required to receive the NQR emissions in the presence of the transmitted excitation signal to prevent self-jamming. Such receivers would be pushing the state of the art. An alternative solution is to provide a method to cancel as much of the transmitted signal as possible before it can enter the receiver but still fully illuminate the suspect material. This lowers the dynamic range requirements of the receiver to standard levels to be able to receive the weak NQR emissions from the explosive materials. This invention comprises a bridge circuit through which the CW excitation signal passes, but yet the receiver, connected across the balanced terminals of the bridge is isolated from the transmitted signal. One side of the bridge connects to the NQR measurement probe while the other side is connected to an impedance machine that balances the bridge.

The ability to perform NQR measurements at human-safe power levels enables the NQR measurement system to be incorporated within an RF-isolated corridor or room or chamber through which could check a person for explosives as that persons walks through a probe. Since most NQR frequencies are below 15 MHz, the hallway would appear as a waveguide operating in cutoff whereby no external man made or atmospheric RF noise could enter while people could pass through walking. Multiple probes could be installed in the hallway to test the passerby at multiple suspected explosive material NQR frequencies.

SUMMARY

The preferred embodiment includes a Nuclear Quadrupole Resonance (NQR) system for detecting at least one material under test (MUT). The NQR system includes a waveform generator configured to generate a continuous wave (CW) input signal at one or more of a set of specified frequencies. A chamber installed with a probe receives at least one MUT that is carried by a person walking through the chamber. The probe, connected to the waveform generator, radiates a CW signal to illuminate the MUT while simultaneously listening with a receiver for an NQR emission. The waveform generator is connected to the NQR probe within the chamber through a balanced bridge circuit whereby one side of the bridge is connected to the probe and the other side is connected to a device capable of creating any impedance to match the impedance of the probe and thus balancing the bridge when there is no NQR emitting material present. The receiver is comprised of a differential amplifier front end that is connected across the balanced arms of the bridge. When a MUT with an NQR emission is present, that bridge arm connected to the probe receives the signal which unbalances the bridge and is detected by the receiver. A detector can then detect the MUT based, at least in part, on the resonance signal.

Another configuration of the preferred embodiment is an NQR measurement system for detecting a material. This measurement system includes an NRQ measurement chamber, a subtractor and a detector. The NQR measurement chamber receives the material as a person carries it through the chamber and an excited response signal is generated responsive to a CW signal transmitted into the chamber and the material. The subtractor generates a difference signal by subtracting a reference signal from response signal. The reference signal represents a CW signal transmitted into the chamber when the chamber is empty and lacking the material. The detector configured detects the material is present in the chamber based, at least in part, on the difference signal that represent the excited signal generated by the MUT.

Another configuration of the preferred embodiment is a method of detecting at least one material using Nuclear Quadrupole Resonance (NQR). The method inputs a continuous wave (CW) signal into an NQR chamber. In general, the chamber is a large waveguide allowing a person carrying a material under test (MUT) to walk/pass through the chamber. A reference signal representative of the chamber without a MUT in the chamber is measured/determined. An excited response signal from the chamber is received that includes the CW signal and at least one excited frequency responsive to the MUT. The reference signal is removed from the response signal to generate an excited difference signal. The material is detected based, at least in part, on whether the excited difference signal exceeds a threshold value. In some versions of the method, an alarm indicator is generated indicating the person associated with the contraband material is passing through the chamber. For example, the alarm can be generated on a screen at an airport to indicate to airport security that the person may have contraband material and that security personnel should take appropriate security precautions and actions.

BRIEF DESCRIPTION OF SEVERAL VIEWS OF THE DRAWINGS

One or more preferred embodiments that illustrate the best mode(s) are set forth in the drawings and in the following description. The appended claims particularly and distinctly point out and set forth the invention.

The accompanying drawings, which are incorporated in and constitute a part of the specification, illustrate various example methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

Similar numbers refer to similar parts throughout the drawings.

DETAILED DESCRIPTION

Figure 1:
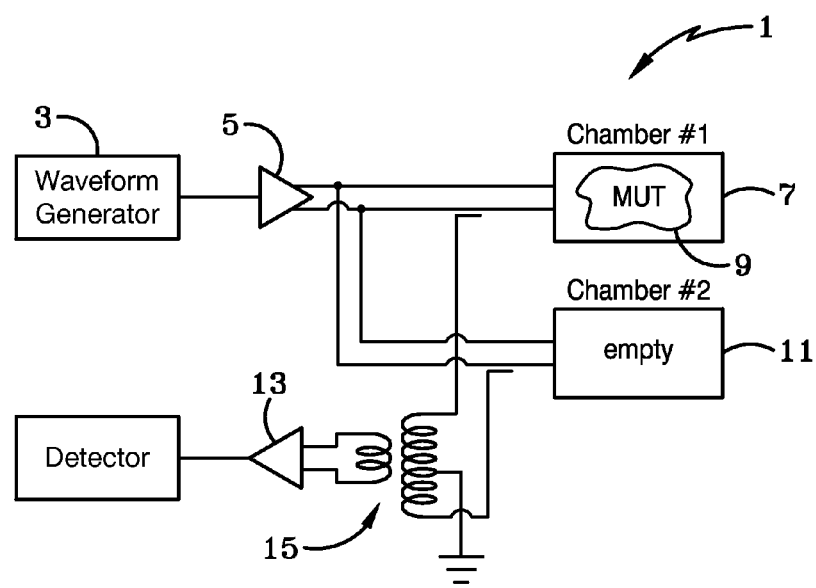
FIG. 1 is a schematic view of an NQR CW measurement system configured to perform a sample embodiment of the present invention using a transformer to cancel the signal that is transmitted to the MUT from being received by the detector thus allowing it to detect the weak NQR emissions from the MUT.
Figure 3:
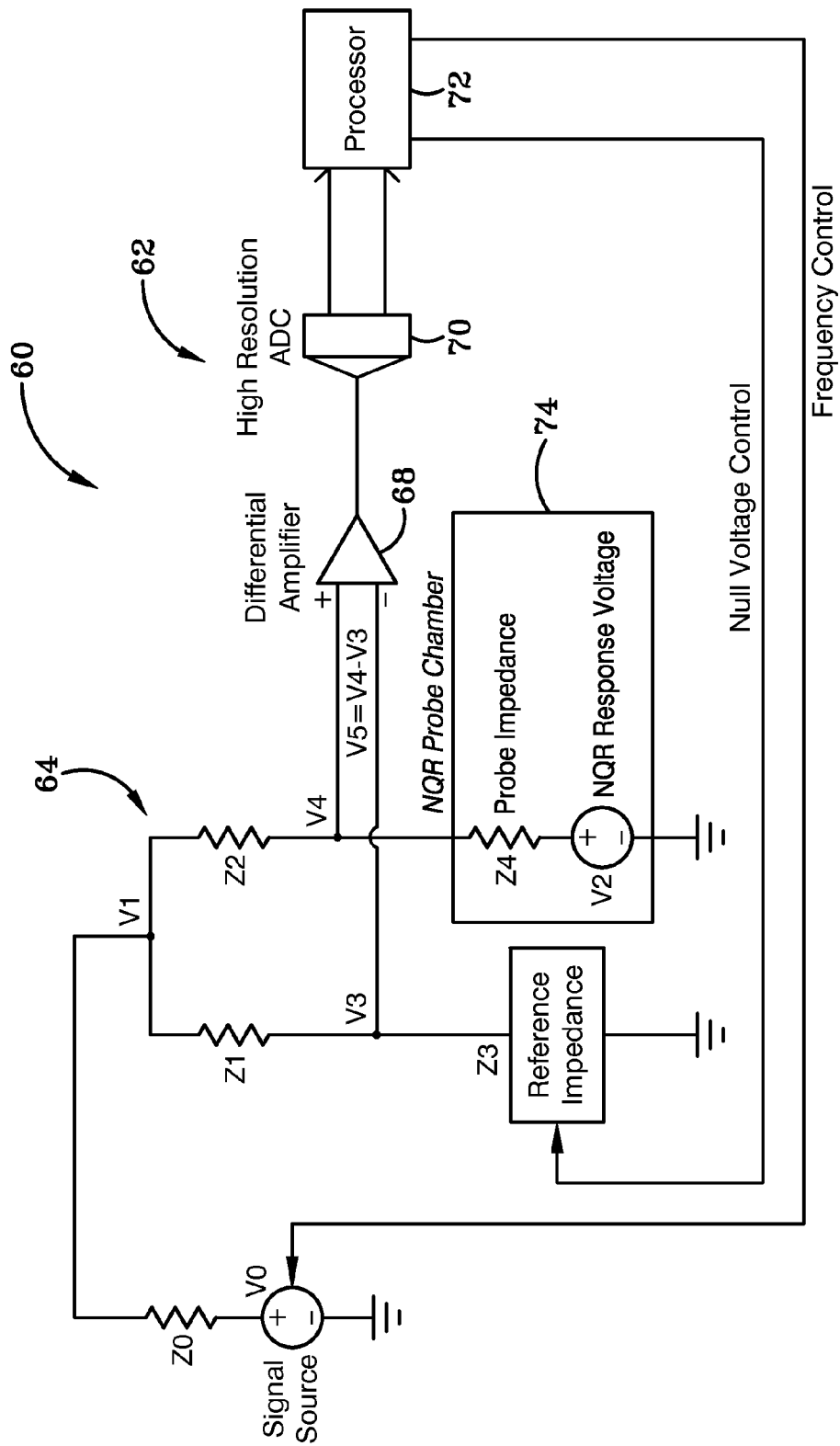
FIG. 3 is a schematic view of a system configured to perform an alternative embodiment of the Nuclear Quadrupole Resonance System of the present invention using a bridge circuit with an impedance machine to balance the bridge.

The NQR systems of this patent application are an improvement of prior art systems because CW signal is input into the novel NQR systems of this patent application without the need to "pulse" the input as in prior art systems. The CW signal is about one watt of power (or other FCC regulated value) so that people may safely pass through an NQR chamber that the CW signal is transmitted into. The CW input signal is generally at a selected frequency between about 200 kHz and 30 MHz. When the input signal excites a material under test (MUT) such as an explosive or other material at its NQR frequency, the MUT releases an NQR emission that contains one or more frequencies responsive to the MUT. FIGS. 1 and 3 illustrate embodiments of novel NQR systems that suppress the CW input signal from entering the receiver/detector to allow very low level emitted by the MUT to be detected. The system in FIG. 1 sends the CW excitation signal on differential transmission lines to probes within two similar test chambers, one that contains the MUT and the other representing the reference load impedance. Directional couplers are connected in series with the signal lines going to each chamber to couple signals reflecting back from the probes in the chambers through a transformer. Similar signals arriving to both terminals of the coil of the transformer primary fail to produce a voltage at the secondary side of the transformer. Differential signals arriving at the primary terminals, however, produce a voltage at the secondary terminals that are amplified and detected. The amount of generator waveform suppression is a function of both the directional coupler isolation and the common mode rejection ratio of the transformer. FIG. 3 cancels out the CW input signal in the response signal by using a reference impedance in a bridge circuit to generate a reference signal that is subtracted from a response signal from the probe in the chamber with the MUT. Both of these figures are discussed further below.

In the system 1 of FIG. 1, a traditional network analyzer is replaced with an arbitrary waveform generator 3 and power splitter/differential RF amplifier 5 that transmits the waveform generator signal to a first chamber 7 in which the material under test (MUT) 9 exists and simultaneously to a second chamber 11 that is an empty chamber which typically has the same configuration as the first chamber 7.

The same continuous wave (CW) signal is injected into both chambers. The signals returned from the probes within the chambers are tapped off the transmission lines through directional couplers 17 and 19 and sent to the two terminals of the primary side of the transformer 15. The common mode signals are not coupled to the secondary side of the transformer while the differential signals are transferred to the secondary terminals of the transformer. The signal at the secondary terminals is amplified through an amplifier 13 and then detected. The detector and amplifier 13 constitute the receiver of the system. In some configurations to the transformer and possibly amplifier 13 can be replaced by a differential amplifier.

Figure 2:
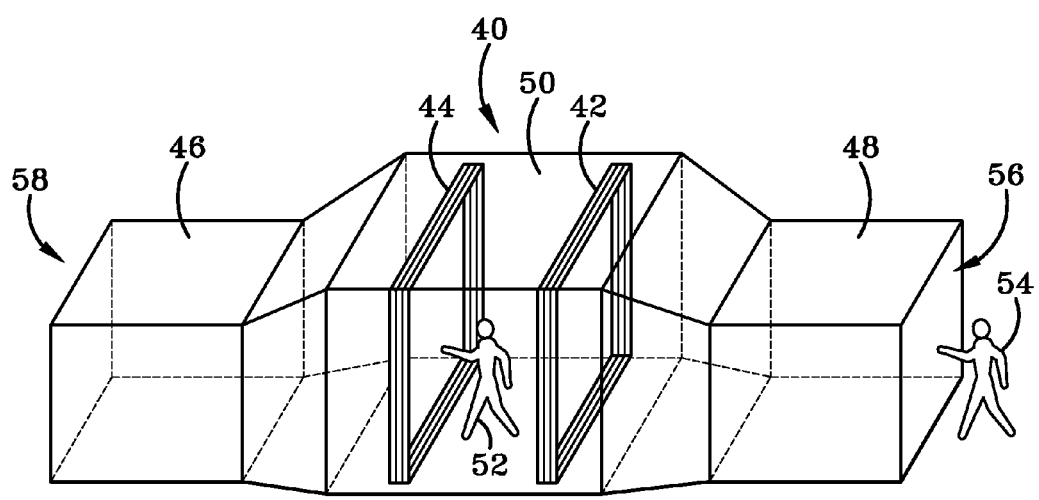
FIG. 2 is a schematic perspective view of a sample system of the invention. This figure shows a shielded measurement chamber large enough to accommodate a person walking through it.

FIG. 2 illustrates a different embodiment of an NQR system that has one RF shielded chamber and hallways 40 with two separate probe stations represented as coils 42, 44 within the chamber. Preferably the coils 42, 44 in operation can generate low impedance RF/magnetic fields. In other configurations, for example, the probe coils could be replaced by vertically running transmission line pairs spaced one from the other or other types of transmission pairs or parallel plates as understood by those of ordinary skill in this art. The chamber 40 may include narrower sections that act as waveguide filters 46 and 48 operating in cutoff that filter outside RF noise from the center portion 50 of the chamber 40. The waveguide filters 46, 48 can, for example, filter such noise with about 8.8 decibels (dB) per meter (m) of attenuation (typically at least 8.0 dB/m). Filters 46 and 48 and the center portion of the chamber 40 essentially form a very large waveguide chamber through which one or more people 52, 54 can walk. As understood by those of ordinary skill in this art, all the main components—such as sidewalls, top walls or ceiling wall, bottom walls or floors, etc.—of the chamber 40 are preferably constructed out of electrically conductive materials, typically sheet metal or metal screen.

In operation, if an individual 52 carrying contraband enters or passes through the first coil 42, the material under test they are carrying will not be picked up by the second coil 44 because the individual and MUT have not yet reached the second coil 44. Therefore the second transmission line 44 can at that time be considered as an empty chamber as discussed above with reference to FIG. 1. When the individual 52 carrying the material under test finishes passing through the first coil or chamber 42 and then passes through the second coil 44, then (as the person and MUT are passing through coil 44) the second coil 44 acts as a chamber that has the material under test in it, with the first chamber being simultaneously empty. In general, the first coil 42 and the second coil 44 spaced apart in system 40 essential creates two waveguide chambers back to back, that is, with one of the chambers downstream of the other chamber such that a person carrying a MUT passes sequentially through the first waveguide chamber 42 and then the second or downstream chamber 44 as the person and MUT move downstream through chamber 40. Alternatively, if a positive detection of an NQR emission at one frequency is made when a person 52 passes through the first coil 42, then a different test frequency might be performed as the person passes through the second coil 44. The identification of two different NQR frequencies from a MUT provides a higher probability that the person is carrying contraband material and it further lower the probability of false positives. To test for more NQR frequencies from a MUT's signature, multiple probe stations could be installed within the chamber.

In the embodiment of FIG. 2, detection of the material under test in one chamber and then in the other chamber, as when an individual walks through the two chambers, is a confirmation of the presence of the material under test. This is because if the material is separately and sequentially detected in both chambers then it is a positive test. Detection of the material by only one of the two chambers—i.e., a detection followed by no detection (or vice versa)—is most likely indicative of a false positive test such that no material is present.

The chambers discussed above may require the detection of very small NQR CW signals at high frequencies and also may require that reflections or active responses from a target be measured at the same time as the target is illuminated. The receiver ideally should be able to detect very low level responses while being illuminated by a very strong excitation signal. For very sensitive receivers, the excitation signal is too strong and saturates the receiver signal whereby the receiver cannot detect the small response signals from the target. Therefore, a receiver/detector with a very high dynamic range (ratio of peak to smallest signal detectable) is typically used to detect very small signals. Radars function by sending strong pulses and detecting very weak responses. Radars have a special advantage in that the target is usually quite far away in terms of wavelengths since most radars operate at microwave frequencies and higher. This allows the radar to send out a pulse, shut down, and then turn on the receiver to get the response. Therefore the receiver is not on at the same time as the transmitter. In cases when the target is much closer, the transmitter and receiver might be on at the same time, but directional devices such as circulators can be used to separate outgoing signals from incoming signals and thus minimize the possibility of the transmitter overloading the receiver amplifier. At high frequencies, circulators which have the amount of isolation needed are generally not available. The wavelength can be kilometers long and hence separation delay is not a feasible option as in radar. A method to minimize the excitation signal to a level where a receiver with standard dynamic range is needed to measure the response signal. Initial assumptions are that the NQR response is between −130 dB to −150 dB below the excitation signal. Hence, if 60 to 70 dB of isolation could be obtained, it would be possible to detect the response with a sensitive receiver having 60 to 80 dB of dynamic range.

A general description of how a NQR system detects chemical compounds on humans is now provided. Chemical compounds of interest have NQR signatures at frequencies as low as a few hundred KHz to low MHz. Medium frequency (MF) to high frequency (HF) noise in that low frequency regime such as originating from lightning, solar atmospheric ionization, meteor tracks, radio stations, power lines, and other man-made noises such as from motors, computers, etc.—is quite high. NQR measurements are generally done in a radio frequency (RF) insulated booth or tunnel to prevent the unwanted atmospheric and man-made noises from corrupting the measurement data.

Description of the Test Chamber

A waveguide has a cutoff wavelength $\lambda_{oc}$ dependent on its dimensions. For wavelengths larger than the cutoff wavelength, the attenuation is given 3 where $$\beta = \frac{2\pi\sqrt{\left(\frac{\lambda_o}{\lambda_{oc}}\right)^2 - 1}}{\lambda_o} \text{ nepers/m}$$

Where:
  $\lambda_o = c/f = 300/f$ meters, and f=frequency (MHz)
The attenuation is given by $$\text{Atten} = 20 \ast \log(e^{\beta x}) = 20 \ast \beta x \ast 0.4343 = 8.686 \ast \beta x \text{ dB/m}$$

In a typical in the example NQR system 40 of FIG. 2, an entrance opening 56 of chamber 40 is formed adjacent an upstream end of upstream filter 46 and an exit opening 56 is formed adjacent a downstream end of downstream filter 48. Entrance and exit opening 56, 58 which are about 8 feet high by 10 feet wide would provide about 8.9 dB/meter attenuation at 4 MHz. Therefore, ten foot long tunnels (filters 46, 48) would provide better than 25 dB isolation from outside noises.

Description of the Bridge Circuit

FIG. 3 illustrates a third sample embodiment as an example of an NQR measurement system 60 that can simultaneously transmit HF signals and detect very small NQR signal emissions. The continuous wave NQR spectrometer 60 of FIG. 3 includes a self-calibrating bridge circuit 64 that cancels the excitation signal while allowing a sensitive digital receiver 62 to detect the NQR response. The system 60 contains a waveform generator signal source V0, a bridge circuit 64, a differential amplifier 68, a high resolution analog-to-digital converter (ADC) 70, a processor 72, a reference impedance Z3 and a probe in a chamber 74 (e.g., NQR probe). The probe and chamber 74 can be represented as a probe impedance Z4 and an NQR response of the MUT as voltage V2.

The bridge circuit 64 consists of the complex impedances Z1, Z2, Z3, and Z4. Z1 and Z2 preferably are resistive and roughly equal to each other; however, they can have different values. Z4 is the impedance of the tunnel probe 74 described above or any other probe used to measure the NQR response. Z3 is the reference impedance and is automatically adjusted to match that of Z4, but more specifically to make V3=V4, thereby driving V5 to zero volts. When V5=0, the common mode driving voltage V0 has been canceled and is not detected by the receiver comprised of 68, 70 and 72.

However, matching Z3 exactly to Z4 is not physically possible throughout the measurement process. This is because Z4 changes as a person walks through the probe and, since the person only walks through the probe once, it is not possible to compare V3 and V4 when the person is carrying the substance of interest (MUT) to when he is not. In a static laboratory measurement, the sample holder would be placed inside the probe chamber and measured over a band of frequencies. The associated reference impedances Z3 would be saved. The compound of interest (MUT) would then be placed into the sample holder, with the assumption that the impedance Z4 is not affected by the introduction of the material, and a rerun would be conducted of the measurements applying the reference values for Z3 that were earlier collected. At the NQR resonant frequency, V2 would appear and detected at V5.

In a dynamic situation with a person walking through the probe chamber, the luxury of making measurements of the person without and with material samples is not available. Therefore, an alternative approach is required to get the reference measurement.

Noting that the NQR resonance is very narrow banded (~100 Hz), the probe is designed to be a non-resonant device whereby the fluctuation in impedance does not change more than a fraction of a percent over a fixed frequency bandwidth of a few kilohertz. The reference measurement is done at a non-NQR resonant frequency. Within the digital signal processor 72, an algorithm such as the LMS, the simplex, the min-max or any other optimization routine adjusts the real and imaginary parts of Z3 such that V5 is driven to a null (zero volts). Z3 can be a variable resistor and a variable capacitor in series, implemented with PIN and varactor diode circuitry. Z3 can also be an impedance machine. These are mixed signal devices with output load terminals whose impedance can be located anywhere within a Smith Chart. A second measurement at the other extreme of the band could be averaged with the first measurement to determine a second complex Z3=R3+jX3 value. Then several measurements over the band in which the NQR resonant frequency is expected to be found are done with Z3 set to the previously calibrated value. When the NQR voltage V2 appears at its resonant frequency if the compound of interest is present, then detection would be made. All these measurements can be performed in a fraction of a second so that the person's motion and location have not changed enough to dynamically change Z4. NQR resonant frequencies for most materials are temperature dependent. Hence, ambient temperature could be monitored along with an infrared (IR) scan to obtain body temperature to determine desired frequency bands over which to perform measurements while the person is walking through the probe chamber.

The fact that Z3 is dynamically mimicking the environment and being adaptively updated by the digital controller produces a noise-riding threshold and constant false alarm rate. The environment may change due to nearby objects or a person's proximity to the probe, and this change is detected by the differential amplifier. Impedance Z3 is readjusted for a null at a non-NQR frequency. The non-NQR frequency is close enough to the NQR frequency so that the difference in probe impedance vs. frequency is less than the difference in signal level produced when the frequency is set to the NQR frequency and material is present.

The system is similar in concept to a Dicke radiometer where small differences in level of S+N (signal plus noise) vs. N (noise only) are AC-coupled to eliminate DC drift and bias, and amplified for detection. Such devices are capable of measuring power levels below thermal noise, limited only by signal processing power and integration time.

Figure 4:
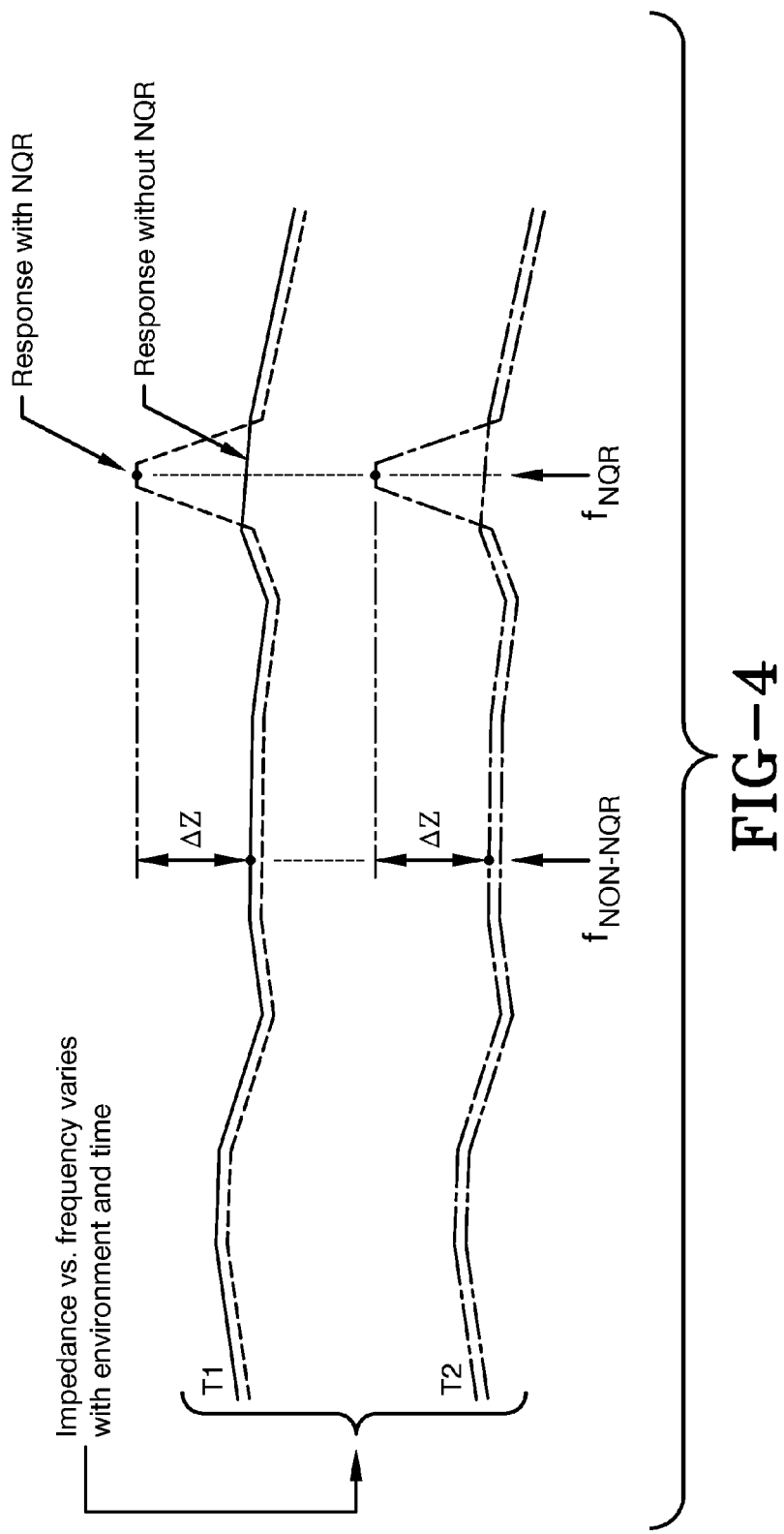
FIG. 4 is a graphical view of a differential impedance measurement with a floating absolute threshold in accordance with an embodiment of the present invention.

FIG. 4 illustrates the concept of a differential impedance measurement with a floating absolute threshold. When $\Delta Z$ exceeds a predetermined threshold, a detection is made. Note that the absolute level of Z3 may drift with time and environment. The time difference between T1 and T2 may be made adaptive.

The processes of common mode signal cancellation is now described. Basic analysis of the circuit in FIG. 3 shows that V5 is given by $$V_5 = V_1 \left[ \frac{Z_4}{Z_2 + Z_4} - \frac{Z_3}{Z_1 + Z_3} \right] - V_2 \left[ \frac{Z_4}{Z_2 + Z_4} \right]$$

The influence of the common mode voltage V1 disappears when $$Z_3 = \frac{Z_1 Z_4}{Z_2}$$

and in the preferred embodiment where Z1 and Z2 are can be selected as resistors. Their values could be selected to scale the probe impedance Z4 to a range where a reasonable circuit to produce reference impedance Z3 can be designed. For example, if Z1=Z2, Z1=0.5*Z3, then Z3=Z4. The amount of common mode voltage V1 cancellation that can be attained will be directly a factor of how close Z3 matches Z4. Furthermore, assuming Z3 can be matched exactly to Z4, the next assumption is that Z4 does not change much from the reference frequency measurement to the actual measurement. For the sake of argument, assume that Z4' becomes (1+α)Z4. Then V5 becomes $$V_5 = V_1 \left[ \frac{\alpha}{3(1.5 + \alpha)} \right] - V_2 \left[ \frac{1 + \alpha}{1.5 + \alpha} \right] \approx V_1 \left[ \frac{\alpha}{4.5} \right] - V_2 \left[ \frac{2}{3} \right]$$

For a 1% change (α=0.01), the suppression of V1 is 53 dB. Therefore, if the ratio of V1 to V2 is 130 dB, then a detection circuit with a dynamic range of at least 77 dB would detect V2, assuming no other noise sources.

Those skilled in the art will appreciate that the apparatus of the invention will reduce the dynamic range requirement by the level of common mode rejection that it can achieve. If a common mode rejection of 70 dB is achieved on a measurement requiring 130 dB, then the range has been reduced to 60 dB. Nevertheless, this does not change the sensitivity required in terms of absolute power levels measured.

Those skilled in the art will also appreciate that the method and apparatus of this invention could also be used for the detection of buried pipes or wires through LF and MF excitation. Low frequency RF can penetrate soil better than radar signals at ultra-high frequency (UHF) and Microwave frequencies. The reflection of RF signals from buried metal conductors can be −80 to −100 dB below the excitation signal at resonance. The use of the common mode rejection circuit would provide the ability to transmit and receive a CW signal simultaneously at these low frequencies.

In some configuration the embodiments discussed above can be used in clandestine environments to detect explosive, drugs and other contraband on people without them even knowing that they are being observed. For example, may airports have short and/or long term parking lots that are connected to long walkways that people must pass through when walking from their car to the airport. It is envisioned that NQR systems such as the system 40 illustrated in FIG. 2 could be built into these walkways/tunnels and disguised as part of those tunnels so that one passing through those walkways would not even suspect that they were being monitored by an NQR system 40. However, security personal would be monitoring those clandestine systems and if there is a possible positive test result for contraband, the person with the possible positive result could then be tracked through video cameras and later security testing and screening could be more focused on those individuals identified by the NQR system(s) 40.

Clandestine types of uses of the NQR measurement systems described above can include uses in screening people entering sports stadiums. NQR systems could also be built into almost any public building and disguised as part of those buildings. Additionally clandestine NQR systems could be built into entrances into subway systems, bus terminals and other transportation systems. Those of ordinary skill in the art will appreciate that the NQR systems discussed above and other variations of them can be used in other environments where it is desirable to find individuals that are carrying contraband such as explosives, drugs and the like.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 5:
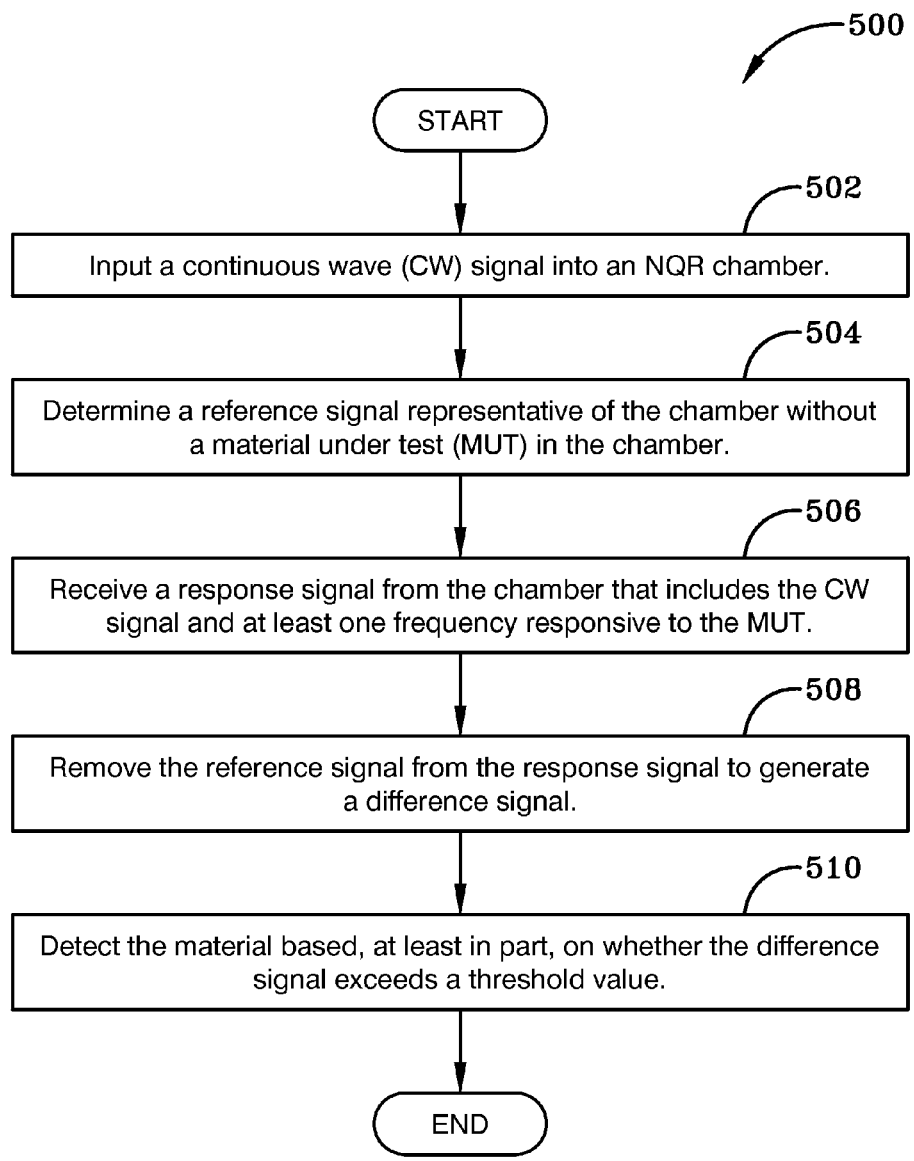
FIG. 5 is a set of method steps according an embodiment of the present invention.

FIG. 5 illustrates a method 500 of detecting at least one material using Nuclear Quadrupole Resonance (NQR). The method 500 inputs, at 502, a continuous wave (CW) signal into an NQR chamber. In general, the chamber is a large waveguide allowing a person carrying a material under test (MUT) to walk/pass through the chamber. A reference signal representative of the chamber without a MUT in the chamber is measured/determined, at 504. This reference signal can be generated using a reference impedance in a bridge as discussed above. A response signal from the chamber is received, at 506, which includes the CW signal and at least one frequency responsive to the MUT. The reference signal is removed from the response signal, at 508, to generate a difference signal. The material is detected based, at least in part, on whether the difference signal exceeded a threshold value, at 510. In some versions of the method, an alarm indicator is generated indicating the person is associated with the contraband material is passing through the chamber.

For example, the alarm can be generated on a screen to indicate to airport security that the person may have contraband material and that security personnel should take appropriate security precautions and actions.

The related and co-owned U.S. Application entitled "METHOD FOR DETECTING TARGET MATERIALS USING NUCLEAR QUADRUPOLE RESONANCE," which is filed contemporaneously herewith, is incorporated herein as if fully rewritten.

In the foregoing description, certain terms have been used for brevity, clearness, and understanding. No unnecessary limitations are to be implied therefrom beyond the requirement of the prior art because such terms are used for descriptive purposes and are intended to be broadly construed. Therefore, the invention is not limited to the specific details, the representative embodiments, and illustrative examples shown and described. Thus, this application is intended to embrace alterations, modifications, and variations that fall within the scope of the appended claims.

Moreover, the description and illustration of the invention is an example and the invention is not limited to the exact details shown or described. References to "the preferred embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in the preferred embodiment" does not necessarily refer to the same embodiment, though it may.

The invention claimed is:

1. A Nuclear Quadrupole Resonance (NQR) measurement system for detecting at least one material under test (MUT), the system comprising:
   a waveform generator configured to generate a continuous wave (CW) input signal comprising one or more frequencies;
   a chamber configured to receive the at least one MUT when carried by a person passing through the chamber;
   a probe configured to excite the MUT and then detect NQR RF emissions from the MUT;
   a bridge circuit configured to subtract a signal representing the CW input signal in the chamber from a response signal that includes the CW input signal and the NQR RF emissions to generate output NQR RF emissions;
   a detector configured to detect the MUT based, at least in part, on the NQR RF emissions; and
   a signal generator configured to generate the CW input signal;
   wherein the bridge circuit further comprises:
   a reference impedance; and
   a resistor connected between the signal generator and the reference impedance, wherein the signal representing the CW input signal is generated at a node between the signal generator and the reference impedance.

2. The NQR measurement system of claim 1 further comprising:
   a processor configured to set a value of the reference impedance.

3. The NQR measurement system of claim 2 wherein the value of the reference impedance represents a value representative of the chamber when the chamber is empty.

4. The NQR measurement system of claim 2 wherein the reference impedance is a complex impedance.

5. The NQR measurement system of claim 1 further comprising:

an amplifier configured to amplify the response signal to create an amplified signal, wherein detector is configured to detect the MUT based, at least in part, on the amplified signal.

6. An NQR measurement system for detecting a material comprising:
   an NQR measurement chamber that is shielded from external RF noises and that is configured to receive the material, wherein an NQR signal is emitted by the material in response to a CW excitation signal transmitted into the chamber and the material;
   a subtractor configured to generate a difference signal by subtracting a reference signal from response signal to generate a difference signal, wherein the reference signal represents a CW signal transmitted into the chamber when the chamber is lacking the material; and
   a detector configured to detect the material is present in the chamber based, at least in part on the difference signal.

7. The NQR measurement system of claim 6 further comprising:
   a bridge configured to generate the reference signal.

8. The NQR measurement system of claim 7 wherein the bridge further comprises:
   a reference impedance configured to generate a voltage that is the reference signal that balances the bridge.

9. The NQR measurement system of claim 6 where subtractor is a differential amplifier.

10. The NQR measurement system of claim 9 wherein the differential amplifier suppresses a common mode signal of the amplifier.

11. The NQR measurement system of claim 9 wherein the differential amplifier is an operational amplifier.

12. The NQR measurement system of claim 6 wherein the detector is configured to detect the material when the difference signal crosses a threshold value.

13. The NQR measurement system of claim 6 wherein the chamber is a first chamber and further comprising:
   a second NQR chamber physically the same as the first chamber, wherein the second NQR chamber lacks the material, and wherein the reference signal is taken from the second chamber.

14. The NQR measurement system of claim 6 wherein the chamber is configured as a metallic waveguide chamber through which the person carrying the material can pass through.

15. The NQR measurement system of claim 6 further comprising:
   an impedance Z1 connected to a generator of the CW input signal;
   an impedance Z2 connected to the generator; and
   an impedance Z3 connected between impedance Z1 and ground so that a voltage representing the reference signal is created between impedance Z1 and impedance Z3; and
   and an NQR probe connected between impedance Z2 and ground, wherein the response signal is located between the NQR probe and Z2.

16. The NQR measurement system of claim 15 wherein impedance Z3 is a reference impedance and further comprising:
   a processor configured to update the reference impedance.

17. A method of detection using Nuclear Quadrupole Resonance (NQR) comprising:
   inputting a continuous wave (CW) signal into an NQR chamber;
   determining a reference signal representative of the CW signal in the chamber without a material under test (MUT) in the chamber;
   receiving a response signal from the chamber that includes the CW signal and at least one frequency responsive to the MUT;
   removing the reference signal from the response signal to generate a difference signal; and
   detecting the material based, at least in part, on whether the difference signal exceeding a threshold value; and
   periodically updating a reference impedance value with a new value, wherein the reference signal is based, at least in part, on the reference impedance value.

18. The method of claim 17 further comprising:
   generating an alarm indicator indicating that the person is associated with the contraband material when contraband material is detected.

* * * * *